(12) United States Patent
Svae

(10) Patent No.: US 8,356,427 B2
(45) Date of Patent: Jan. 22, 2013

(54) FOOT SUPPORT DEVICE AND METHOD

(75) Inventor: Bjorn Svae, Olympia, WA (US)

(73) Assignee: GRD Biotech, Inc., Olympia, WA (US)

( * ) Notice: Subject to any disclaimer, the term of this patent is extended or adjusted under 35 U.S.C. 154(b) by 717 days.

(21) Appl. No.: 11/861,194

(22) Filed: Sep. 25, 2007

(65) Prior Publication Data

US 2008/0072455 A1 Mar. 27, 2008

Related U.S. Application Data

(60) Provisional application No. 60/847,340, filed on Sep. 25, 2006.

(51) Int. Cl.
*A43B 7/14* (2006.01)
*A43B 7/22* (2006.01)
*A61F 5/14* (2006.01)

(52) U.S. Cl. ................. 36/71; 36/88; 36/180; 36/140

(58) Field of Classification Search ............. 36/88, 94, 36/106, 140, 144, 8.1, 4, 51, 58.5, 58.6, 72 R, 36/76 R, 7.3, 59 C, 103, 113, 180, 71; D2/961
See application file for complete search history.

(56) References Cited

U.S. PATENT DOCUMENTS

| | | |
|---|---|---|
| 353,910 A | 12/1886 | Zacharie |
| 679,947 A | 8/1901 | Collins |
| 841,732 A | 1/1907 | Smith |
| 1,039,396 A | 9/1912 | Hilgert |
| 1,554,883 A | 9/1925 | Sahlin |
| 1,617,132 A | 2/1927 | Morin |
| 1,642,764 A | 9/1927 | Brown |
| 1,756,587 A | 4/1930 | Durkee |
| 1,847,973 A | 3/1932 | Morton |
| 1,996,215 A | 4/1935 | Sabiston |
| 2,052,115 A | 8/1936 | Shulman |
| 2,207,833 A | 7/1940 | Stark |
| 2,423,622 A | 7/1947 | Samblanet |
| 2,475,417 A * | 7/1949 | Wysowski ................. 36/145 |

(Continued)

FOREIGN PATENT DOCUMENTS

CH 241398 7/1946

(Continued)

OTHER PUBLICATIONS

Natale, J., "Wedges and Corrections for Various Cases of Pronations," The Master Shoe Rebuilder X(2):16, Oct. 1950.

(Continued)

*Primary Examiner* — Jila M Mohandesi
(74) *Attorney, Agent, or Firm* — Christensen O'Connor Johnson Kindness PLLC

(57) ABSTRACT

A foot support adapted to position a foot in an anatomically functional position is provided. The foot support includes a metatarsal portion, a toe portion, and a bendable joint defined between the metatarsal portion and the toe portion. The metatarsal portion is adapted to align the first metatarsal head of a foot, and the metatarsal portion includes an upper surface and a lower surface. The toe portion extends away from the metatarsal portion and is adapted to align the big toe of a foot. The toe portion also includes an upper surface and a lower surface.

6 Claims, 5 Drawing Sheets

U.S. PATENT DOCUMENTS

| | | | |
|---|---|---|---|
| 2,528,082 A | 10/1950 | Rubico | |
| 2,616,190 A | 11/1952 | Darby | |
| 2,737,671 A | 3/1956 | Hill | |
| 2,933,833 A | 4/1960 | Fiorillo | |
| 2,985,970 A * | 5/1961 | McCarthy | 36/11.5 |
| 3,143,812 A * | 8/1964 | Bittner | 36/44 |
| 3,663,978 A | 5/1972 | Meszaros | |
| 3,742,627 A | 7/1973 | Schneider | |
| 4,360,027 A | 11/1982 | Friedlander | |
| 4,408,402 A * | 10/1983 | Looney | 36/43 |
| 4,642,911 A | 2/1987 | Talarico, II | |
| 4,676,801 A | 6/1987 | Lundeen | |
| 5,058,585 A | 10/1991 | Kendall | |
| 5,205,071 A * | 4/1993 | Hergenroeder | 36/8.1 |
| 5,327,663 A | 7/1994 | Pryce | |
| 5,327,664 A | 7/1994 | Rothbart | |
| 5,572,808 A | 11/1996 | Birke | |
| 5,881,478 A * | 3/1999 | McMahon et al. | 36/144 |
| 6,092,314 A | 7/2000 | Rothbart | |
| 6,182,380 B1 | 2/2001 | Liley | |
| 6,212,723 B1 | 4/2001 | Rothbart | |
| 6,412,198 B1 | 7/2002 | Rothbart | |
| 6,694,648 B2 * | 2/2004 | Eriksen | 36/145 |
| 6,938,363 B1 | 9/2005 | Clough | |
| 7,278,226 B2 * | 10/2007 | Holden et al. | 36/35 R |
| 7,832,119 B2 | 11/2010 | Gilmore | |
| 2006/0155233 A1 | 7/2006 | Huber | |

FOREIGN PATENT DOCUMENTS

| | | |
|---|---|---|
| DE | 288914 | 6/1914 |
| DE | 10015534 A | 10/2001 |
| FR | 1111706 | 3/1956 |
| FR | 2652260 A1 | 3/1991 |

OTHER PUBLICATIONS

PCT International Search Report and Written Opinion dated Aug. 21, 2008, issued in corresponding Application No. PCT/US2008/057731, filed Mar. 20, 2008.

Rothbart, B.A., and L. Estabrook, "Excessive Pronation: A Major Biomechanical Determinant in the Development of Chondromalacia and Pelvic Lists," Journal of Manipulative and Physiological Therapeutics 11(5): 373-379, Oct. 1988.

Rothbart, B.A., et al., "Resolving Chronic Low Back Pain: The Foot Connection," American Journal of Pain Management 5(3):73, 84-90, Jul. 1995.

Rothbart, B.A., and M.K. Yerratt, "An Innovative Mechanical Approach to Treating Chronic Knee Pain: A Bio-Implosion Model," American Journal of Pain Management 4(3):123-127, Jul. 1994.

\* cited by examiner

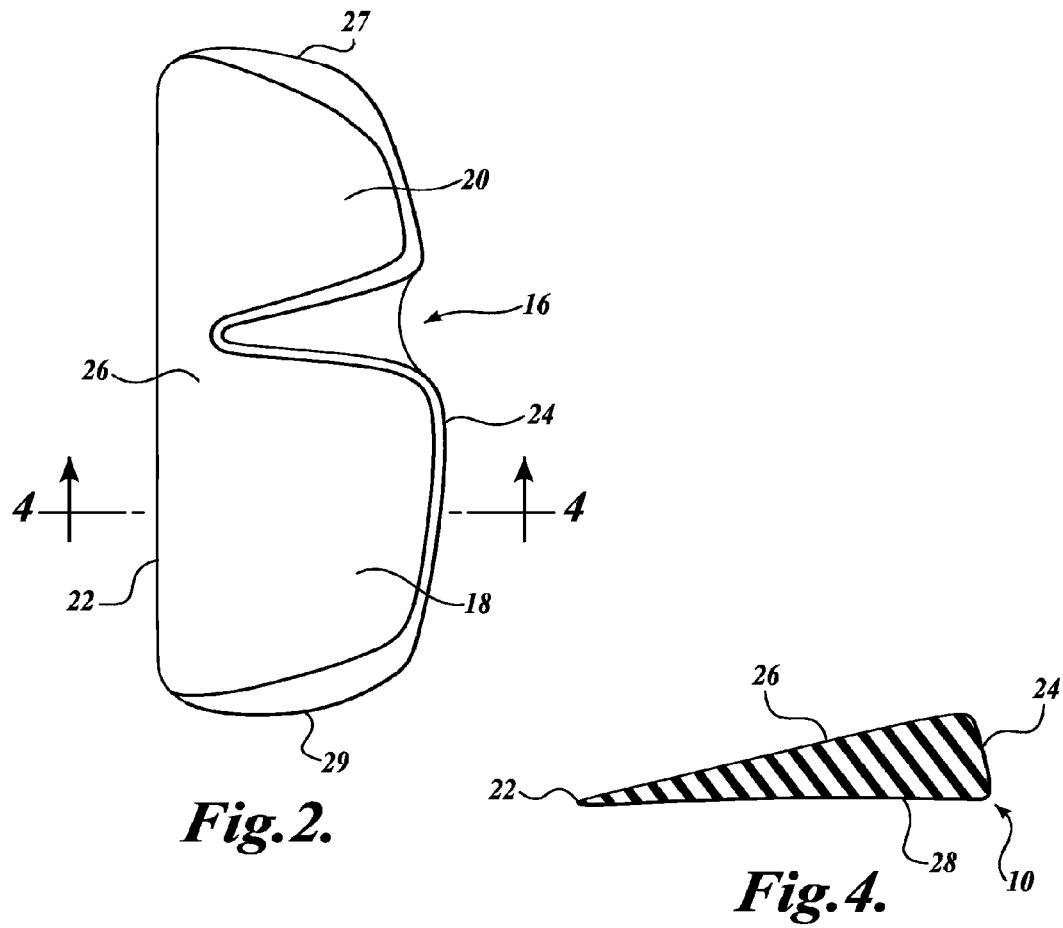
Fig.2.
Fig.4.
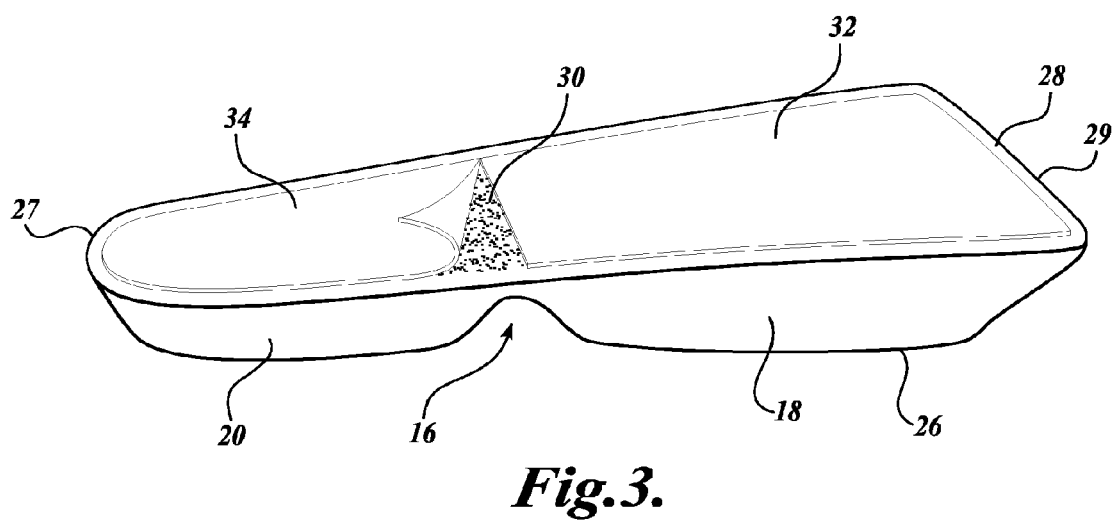
Fig.3.

FOOT SUPPORT DEVICE AND METHOD

CROSS-REFERENCE TO RELATED APPLICATION

This application claims the benefit of U.S. Provisional Application No. 60/847,340, filed Sep. 25, 2006, the disclosure of which is hereby expressly incorporated by reference.

BACKGROUND

The joints and muscles of the body function most efficiently when they are in physical balance. Abnormal movements in one line of the body can interfere with proper movements in other joints. For instance, during walking, the foot transfers the weight of the body to the ground and propels the body, which subjects the body to natural forces and postures that can inflict mechanical stress and strain throughout the interrelated chain of joints, ligaments, muscles, and tendons. When foot imbalance is present, there is a negative impact on the feet, legs, hips, back, and cranium.

Imbalance is often caused by excessive pronation of the foot, or "hyperpronation." Hyperpronation of the foot is the inward, forward and downward twisting of the forefoot relative to the ground. Hyperpronation can cause the framework of the foot to collapse, which can cause plantar fasciitis, heel spurs, tendonitis, bunions, etc., as well as symptoms extrinsic to the foot such as knee pain and low back pain.

To treat and support a hyperpronating foot, foundational stability is provided by maximizing foot-to-ground contact so that the forefoot does not collapse. Traditionally, this is accomplished by using orthotic devices or corrective shoes. In particular, orthotics for supporting a hyperpronating forefoot are designed to support deficits in a foot's contact with the ground, and in essence function so as to build the ground up to the forefoot.

Currently available insoles or orthotics are practical for most closed shoes and for shoes with a lip in the heel that will retain the orthotic within the shoe. During mild and warm weather, many people want to wear open-toed shoes and sandals, and the only option is to glue the orthotic to the shoe permanently. Many people also want to change shoes several times a day, so unless they have orthotics in all of their shoes, they must switch the orthotics from shoe to shoe, which is time consuming and impractical.

Thus, it is desired to have a low-cost orthotic that can be used in a variety of different shoes while providing stabilization to the foot.

SUMMARY

A foot support adapted to position a foot in an anatomically functional position is provided. The foot support includes a metatarsal portion, a toe portion, and a bendable joint defined between the metatarsal portion and the toe portion. The metatarsal portion is adapted to align the first metatarsal head of a foot, and the metatarsal portion includes an upper surface and a lower surface. The toe portion extends away from the metatarsal portion and is adapted to align the big toe of a foot. The toe portion also includes an upper surface and a lower surface.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of the present disclosure will become more readily appreciated by reference to the following detailed description, when taken in conjunction with the accompanying drawings, wherein:

FIG. 2 is a top view of the foot support of FIG. 1;

FIG. 3 is an isometric view of the foot support of FIG. 1;

FIG. 4 is cross-sectional view of the foot support of FIG. 2, taken substantially across line 4-4;

DETAILED DESCRIPTION

Figure 1:
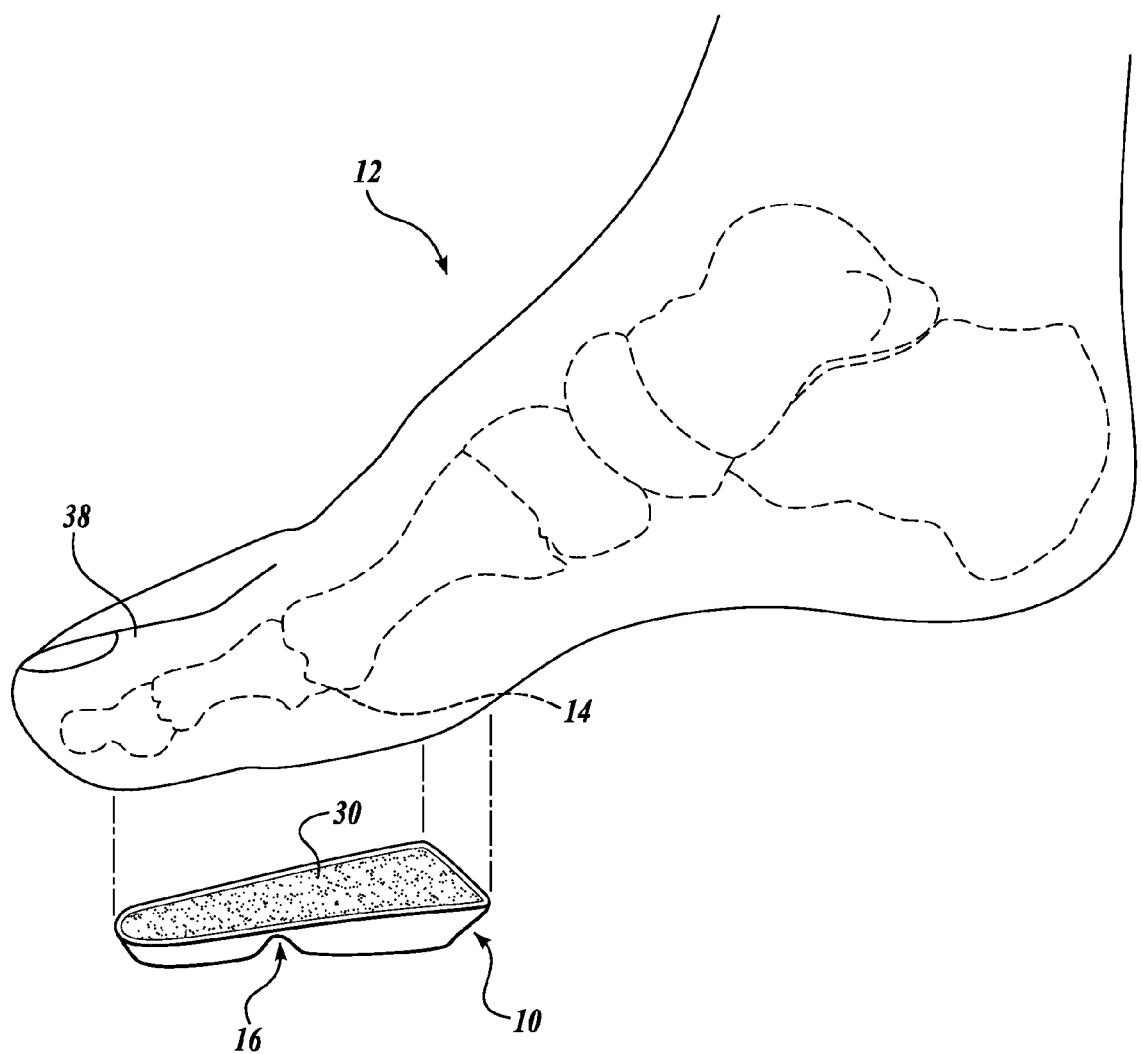
FIG. 1 is an environmental view of a representative embodiment of a foot support constructed in accordance with one embodiment of the present disclosure, wherein the foot support is being mounted to the bottom of a foot.

A disposable orthotic, or foot support 10 shown in accordance with one embodiment of the present disclosure is best seen by referring to FIG. 1. The foot support 10 is attachable to the bottom of a foot 12 or the insole 40 of a shoe (see FIG. 6). When attached to the foot 12 or insole 40 or shoe, the foot support 10 compensates for an elevated first metatarsal 14 and helps correct the user's gait and posture. The foot support 10 functions as an integral part of the foot 12 or shoe so that it may be used with open-toed shoes or without any shoes at all (if worn on the foot).

Referring to FIGS. 2 and 3, the foot support 10 will now be described in greater detail. A bendable joint 16 formed within the foot support 10 divides the foot support 10 into a metatarsal portion 18 and a toe portion 20. The bendable joint 16 is preferably an area of thinner or "cut-out" material within the foot support 10 that generally separates the metatarsal portion 18 from the toe portion 20. The bendable joint 16 allows the foot support 10 to be flexed and bent about a transverse axis generally defined by the area between the metatarsal portion 18 and the toe portion 16. It should be appreciated that the bendable joint 16 may instead be formed in any other well known manner. As non-limiting examples, the bendable joint 16 may instead be formed by creating a partial gap in material between the metatarsal portion 18 and the toe portion 16, by perforating the material between the metatarsal portion 18 and the toe portion 16, etc.

As can best be seen by referring to FIGS. 2 and 4, the foot support 10 includes an upper surface 26, an upper edge 27, a lower surface 28, a lower edge 29, an inner or substantially straight edge 22, and an outer or curved edge 24. The foot support 10 gradually decreases in thickness from the curved edge 24 to the substantially straight edge 22. Preferably, the upper surface 26 slopes downward linearly, such that the foot support 10 is wedge-shaped in cross-section. However, it should be appreciated that other cross-sectional shapes may instead be used, such as rectangular or trapezoidal. The foot support 10 preferably includes angled edges to create a more comfortable wedge-shaped foot support 10. Moreover, the upper surface 26 or lower surface 28 may be concave, convex, or any other suitable shape to conform to the shape of the foot and/or provide added comfort to the user.

As shown in FIG. 3, the foot support 10 also gradually increases in thickness from the upper edge of the toe portion 20 to the lower edge of the metatarsal portion 18 to similarly define a wedge-like shape between the upper and lower edge of the foot support 10. Again, it should be appreciated that other shapes may instead be used, such as rectangular or trapezoidal.

An adhesive 30 is applied to the lower surface 28, which is covered by first and second peel sheets 32 and 34 on the metatarsal portion 18 and the toe portion 20, respectively. The adhesive 30 is sufficiently strong to couple the foot support 10 to the bottom of a user's foot, the insole 40 of a shoe, or another portion of a shoe for a substantial period of time while withstanding moisture and heat. However, the adhesive is also sufficiently weak to be easily removed from a user's foot, insole 40, or shoe without damaging the skin, insole 40, or shoe.

Figure 5:
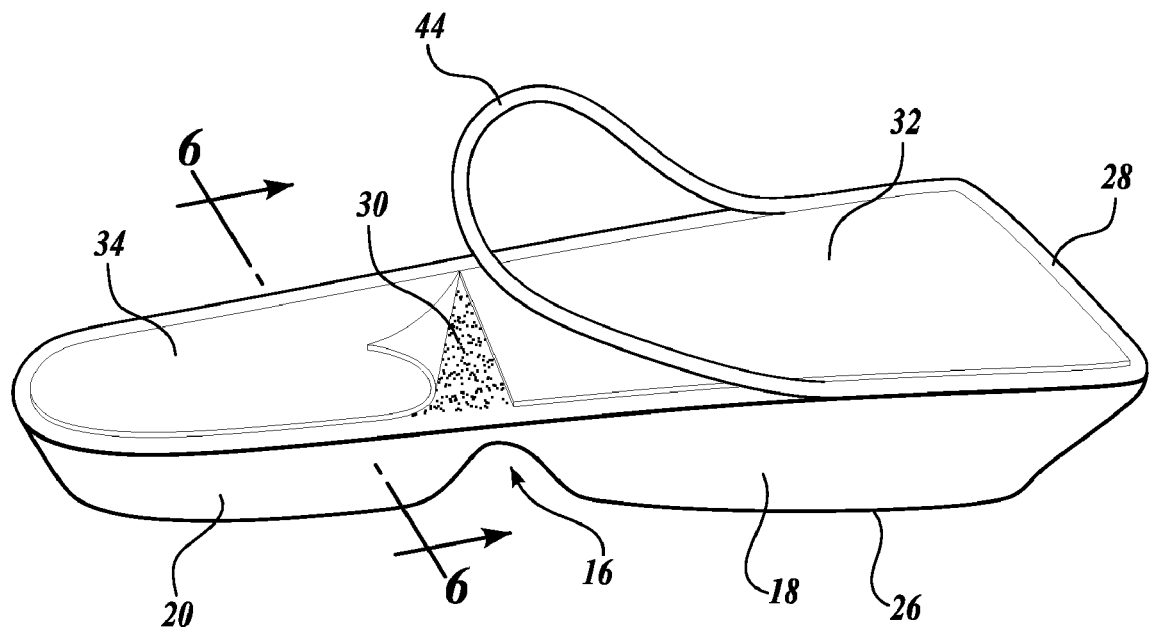
FIG. 5 is an alternate embodiment of the foot support of FIG. 1.
Figure 6:
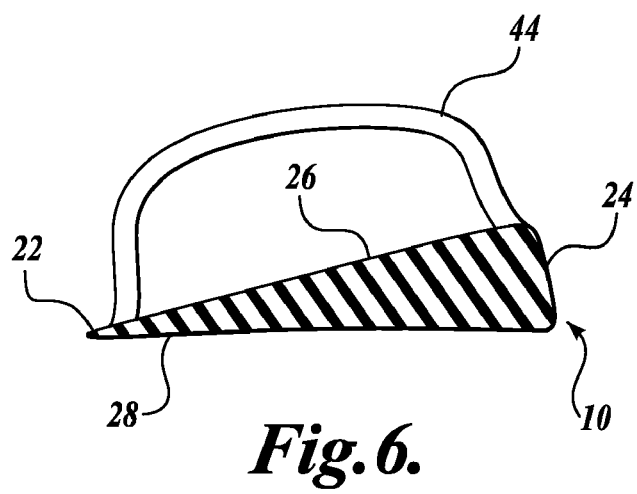
FIG. 6 a cross-sectional view of the foot support of FIG. 5, taken substantially across line 6-6.
Figure 7:
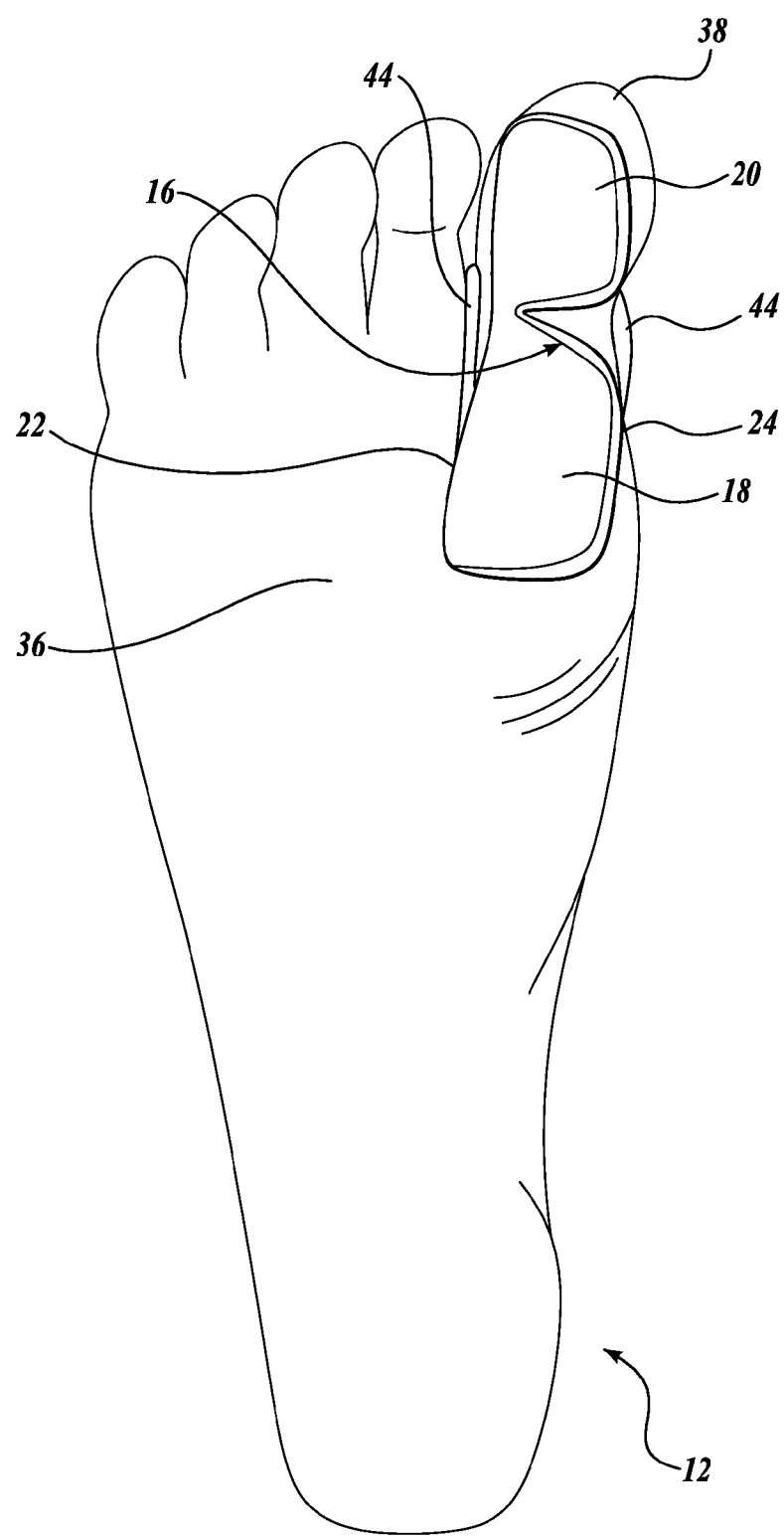
FIG. 7 is an isometric view of the disposable orthotic of FIG. 1 coupled to a foot bottom.
Figure 8:
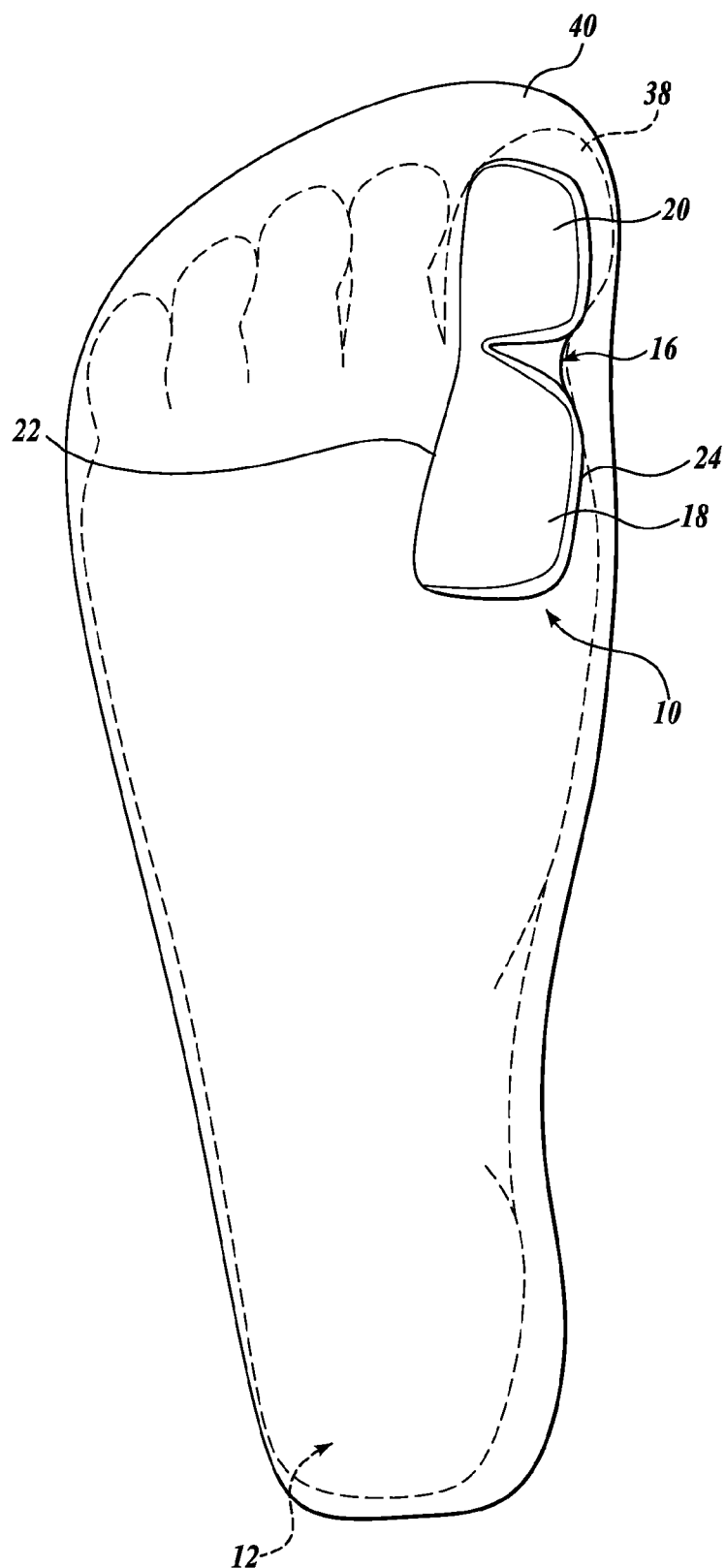
FIG. 8 is an isometric view of the disposable orthotic of FIG. 1 coupled to an insole of a shoe.

Although the foot support 10 is depicted having an adhesive 30 for connection to a foot, other methods of attachment to a foot are also within the scope of the present disclosure. For example, as shown in FIGS. 5 and 6, a loop 44 may be secured to the foot support 10 or integrally formed thereon, wherein the loop 44 is adapted to pass around a portion of the foot. Referring to FIG. 7, the loop 44 may pass around the big toe 38 of the foot 12 to secure the foot support 10 to the foot 12. The loop 44 may be formed in addition to or in lieu of the adhesive 30.

As yet another example, a separate elastic band or piece of material (not shown) may be passed around the big toe 38 and the foot support 10 after the foot support 10 is positioned against the bottom of the foot 12. The elastic may be disposed within the groove defined by the bendable joint 16 to secure the elastic in place and prevent movement of the elastic or the foot support 10 during walking.

The foot support 10 may be composed of any suitable flexible material, such as plastic, (poly vinyl chloride, ethylene vinyl acetate, etc.), rubber, or other well-known materials. The material should be flexible such that the foot support 10 may substantially conform to the bottom of the user's foot in a comfortable manner. The material should also be durable and able to withstand heat and moisture for a substantial period of time; however, the material should not be so expensive that it would preclude the foot support 10 from being used in a disposable manner if needed. Moreover, the material may be covered with a fabric or other material to provided added comfort.

Now referring to FIG. 4, the foot support 10 is coupled to the foot bottom 36 near the big toe 38. The foot support 10 is first positioned on the foot 12 with the lower surface 28 abutting the foot bottom 36 such that the metatarsal portion 18 substantially aligns the first metatarsal head 14 (see FIG. 1), and the toe portion 20 substantially aligns the big toe 38. Moreover, the curved edge 24 follows the contour of the medial side of the foot 12.

After positioning the foot support 10 on the foot 12, the metatarsal portion 18 or toe portion 20 is bent upwardly about the bendable joint 16 so that either the first or second peel sheets 32 or 34, respectively, may be removed. The portion of the foot support 10 with the exposed adhesive 30 is then pressed against the foot bottom 36 to secure that portion to the foot 12. The other of the metatarsal portion 18 or toe portion 20 is then bent upwardly about the bendable joint 16 so that other of the first or second peel sheets 32 or 34 may be removed. The portion of the foot support 10 with the exposed adhesive 30 is then pressed against the foot bottom 36 to secure the foot support 10 to the foot 12.

With the foot support 10 positioned on the foot 12 as described above, the foot support 10 effectively supports the foot 12 in an anatomically efficient and more balanced position. The foot support 10 is active during the last stance of the gait cycle, or "toe-off," and provides support beneath the first metatarsal head 14 to direct the foot 12 to move in a linear fashion and prevent the foot 12 from twisting when weight is transferred forward over the foot 12. The wedge shape of the foot support 10 also stabilizes the foot 12 and reduces hyperpronation, thereby minimizing foot, knee, and lower back problems.

Referring to FIG. 6, the foot support 10 may also be coupled to the insole 40 of a shoe or another suitable portion of a shoe near the placement of the big toe 38. The foot support 10 is positioned on the insole 40 with the lower surface 28 abutting the insole 40. The placement of the foot support 10 is adjusted until the metatarsal portion 18 is positioned to engage the first metatarsal head 14, the toe portion 20 is positioned to engage the big toe 38, and the curved edge 24 is positioned to substantially align the medial edge of the foot 12 when the shoe is placed on the foot 12.

After positioning the foot support 10 on the insole 40, the metatarsal portion 18 or toe portion 20 is bent upwardly about the bendable joint 16 so that either the first or second peel sheets 32 or 34, respectively, may be removed. The portion of the foot support 10 with the exposed adhesive 39 is then pressed against the insole 40 to secure that portion to the insole 40. The other of the metatarsal portion 18 or toe portion 20 is then bent upwardly about the bendable joint 16 so that other of the first or second peel sheets 32 or 34 may be removed. The portion of the foot support 10 with the exposed adhesive 39 is then pressed against the insole 40 to secure the foot support 10 to the insole 40. With the foot support 10 positioned on the insole 40 or on another portion of the shoe as such, the foot support 10 effectively supports the foot 12 in an anatomically beneficial position, as described above.

While the preferred embodiment of the invention has been illustrated and described, it will be appreciated that various changes can be made therein without departing from the spirit and scope of the present disclosure.

The invention claimed is:

1. A foot support adapted to position a foot in an anatomically functional position, the foot support comprising:
   (a) a metatarsal portion sized and shaped to align with the first metatarsal head of a foot, the metatarsal portion having an upper surface and a lower surface, the metatarsal portion defining a lower edge;
   (b) a toe portion extending away from the metatarsal portion, the toe portion sized and shaped to align with the big toe of a foot, the toe portion having an upper surface and a lower surface, the toe portion defining an upper edge opposite the lower edge;
   (c) an inner edge extending between the upper and lower edges and along the metatarsal portion and the toe portion and an outer edge extending between the upper and lower edges and along the metatarsal portion and toe portion and opposite the inner edge, wherein the foot support decreases in thickness from the outer edge to the inner edge; and
   (d) a bendable joint defined between the metatarsal portion and the toe portion, the bendable joint defined in part by a portion of decreased thickness of material between the metatarsal portion and the toe portion, the portion of decreased thickness of material extending from the outer edge toward the inner edge and terminating at a predetermined location between the outer and inner edges but not intersecting the inner edge.

2. The foot support of claim 1, wherein the foot support increases in thickness from the upper edge to the lower edge.

3. The foot support of claim 1, further comprising an adhesive disposed on the lower surface of the metatarsal portion and the lower surface of the toe portion.

4. The foot support of claim 1, wherein the foot support is securable to the bottom of a foot such that the lower surface of the metatarsal portion is secured beneath the first metatarsal of the foot and the lower surface of the toe portion is secured beneath the big toe of the foot.

5. The foot support of claim 1, wherein the foot support is securable within a shoe such that the metatarsal portion is positioned beneath the first metatarsal of the foot and the toe portion is positioned beneath the big toe of the foot.

6. The foot support of claim 1, further comprising a loop secured to the foot support, the loop configured to pass around the big toe of a foot when the metatarsal portion is positioned beneath the first metatarsal of the foot and the toe portion is positioned beneath the big toe of the foot.

* * * * *